United States Patent
Hughes (10) Patent No.: US 11,464,880 B2
(45) Date of Patent: Oct. 11, 2022

(54) DOOR HANDLE DISINFECTION SYSTEM

(71) Applicant: RAYTHEON COMPANY, Waltham, MA (US)

(72) Inventor: Tadd Bernard Hughes, Andover, MA (US)

(73) Assignee: RAYTHEON COMPANY, Waltham, MA (US)

( * ) Notice: Subject to any disclaimer, the term of this patent is extended or adjusted under 35 U.S.C. 154(b) by 84 days.

(21) Appl. No.: 17/078,500

(22) Filed: Oct. 23, 2020

(65) Prior Publication Data

US 2022/0125976 A1 Apr. 28, 2022

(51) Int. Cl.
*A61L 2/24* (2006.01)
*A61L 2/10* (2006.01)
*E05B 1/00* (2006.01)

(52) U.S. Cl.
CPC ..................... *A61L 2/24* (2013.01); *A61L 2/10* (2013.01); *E05B 1/0069* (2013.01); *A61L 2202/11* (2013.01); *A61L 2202/14* (2013.01); *E05Y 2800/40* (2013.01); *E05Y 2900/132* (2013.01)

(58) Field of Classification Search
CPC .......... A61L 2/24; A61L 2/10; A61L 2202/11; A61L 2202/14; E05B 1/0069; E05Y 2800/40; E05Y 2900/132
USPC ........................... 250/453.11, 454.11, 455.11
See application file for complete search history.

(56) References Cited

U.S. PATENT DOCUMENTS

| | | | |
|---|---|---|---|
| 6,298,521 B1 | 10/2001 | Butterfield | |
| 7,598,501 B2 | 10/2009 | Jones | |
| 9,649,398 B1 | 5/2017 | York | |
| 10,092,669 B2 | 10/2018 | Marshall | |
| 2012/0305804 A1 | 12/2012 | Goldman | |
| 2018/0339075 A1 | 11/2018 | Kennedy et al. | |
| 2019/0091358 A1 | 3/2019 | Liao et al. | |
| 2021/0347048 A1* | 11/2021 | Trevor | G02B 3/08 |
| 2021/0353786 A1* | 11/2021 | Crosby | A61L 2/0047 |

FOREIGN PATENT DOCUMENTS

| | | |
|---|---|---|
| DE | 102011001093 A1 | 9/2012 |
| DE | 202015001059 U1 | 5/2015 |
| EP | 2314802 B1 | 5/2014 |
| JP | 5709120 B2 | 4/2015 |
| JP | 2020022715 A | 2/2020 |
| KR | 100998473 B1 | 12/2010 |
| KR | 101900067 B1 | 9/2018 |
| KR | 102167793 B1 | 10/2020 |
| WO | 2019234064 A2 | 12/2019 |

OTHER PUBLICATIONS

International Search Report and Written Opinion in International Patent Application No. PCT/US2021/051673 dated Feb. 2, 2022.

* cited by examiner

*Primary Examiner* — Nicole M Ippolito

(74) *Attorney, Agent, or Firm* — Lando & Anastasi, LLP (57) ABSTRACT

Sterilization assemblies and self-sterilizing systems using the same include a support housing, a plurality of light-emitting diodes coupled to the support housing to selectively emit UV radiation to sterilize contaminants on a door handle, and a controller coupled to a power source and being configured to operate the plurality of light-emitting diodes by selectively providing power to the plurality of light-emitting diodes based on motion detection within a proximity of the door handle.

16 Claims, 8 Drawing Sheets

DOOR HANDLE DISINFECTION SYSTEM

BACKGROUND

To prevent the spread of bacteria, viruses, germs, and other contaminants between door handles and individuals, prior systems have been developed to disinfect the door handles between uses. In some instances, these prior systems periodically sprayed the door handles with a liquid chemical solution designed to disinfect the door handles between uses. Other solutions include avoiding the door handle all together by attaching a fixed bracket to a lower portion of a door for a user to manipulate with their foot.

SUMMARY

Aspects and embodiments are directed to sterilization assemblies and self-sterilizing systems for disinfecting door handles.

According to one embodiment, a sterilization assembly comprises a support housing, a plurality of light-emitting diodes coupled to the support housing, the plurality of light-emitting diodes being configured to selectively emit radiation having at least one wavelength between 100 nm and 400 nm, a controller coupled to the plurality of light-emitting diodes, the controller being configured to operate the plurality of light-emitting diodes by selectively providing power to the plurality of light-emitting diodes, and a power port coupled to a power supply and the controller, the port being configured to provide power to the controller.

In one example, the sterilization assembly further comprises a motion detector coupled to the controller and an I/O port coupled to the motion detector, the controller further being configured to control the motion detector through the I/O port to detect motion within a proximity of the sterilization assembly, and in response to detecting the motion, cease providing power to the plurality of light-emitting diodes.

In another example, the motion detector comprises i) at least one passive infrared sensor (PIR) configured to detect infrared radiation within a field of view of the at least one PIR sensor, the controller is further configured to cease providing power to the plurality of light-emitting diodes in response to the detected infrared radiation, or ii) a capacitive sensor on a surface of the support housing configured to detect a user touching the capacitive sensor or being in a proximity to the capacitive sensor, the capacitive sensor being provided in addition to the at least one PIR sensor, the controller further being configured to cease providing power to the plurality of light-emitting diodes in response to the capacitive sensor detecting the user.

In one example, the motion detector further comprises i) an ultrasonic transducer configured to emit an ultrasonic wave within a field of view of the transducer and detect the ultrasonic wave reflected from an object within the field of view of the transducer, the controller further configured to cease providing power to the plurality of light-emitting diodes in response to the reflected ultrasonic wave being detected, ii) a camera configured to acquire an image within a field of view of the camera, the controller further configured to cease providing power to the plurality of light-emitting diodes in response to processing the image, or iii) a capacitive sensor provided below a surface of the support housing and configured to detect a user touching the surface or being in a proximity to the capacitive sensor, the capacitive sensor being provided in addition to one of the ultrasonic transducer and the camera, the controller further configured to cease providing power to the plurality of light-emitting diodes in response to the capacitive sensor detecting the user.

In another example, the support housing has a circular shape configured to fit around a door knob and transmit the radiation onto a gripping surface of the door knob.

In one example, the support housing is constructed of a material configured to transmit the radiation from the plurality of light emitting diodes to a gripping surface of the sterilization assembly; and wherein the material is: i) rigid or flexible and configured to expand to at least an outermost width of a surface of the gripping surface; and ii) transparent or translucent.

In another example, the sterilization assembly further comprises a hinge configured to join a first section of the support housing to a second section of the support housing, and a separating connector configured to releasably attach the first section to the second section.

In one example, each of the plurality of light-emitting diodes is configured to selectively emit radiation having a wavelength between 100 nm and 280 nm, 280 nm and 315 nm, and/or a wavelength between 315 nm and 400 nm, and the controller is further configured to flash each the plurality of light-emitting diodes at each emitted wavelength for at least a pre-determined period of time.

In another example, at least one of plurality of light-emitting diodes is configured to selectively emit radiation having a wavelength between 100 nm and 280 nm, at least one of the plurality of light-emitting diodes is configured to selectively emit radiation having a wavelength between 280 nm and 315 nm, and at least one of the plurality of light-emitting diodes is configured to emit radiation having a wavelength between 315 nm and 400 nm, and the controller is further configured to emit the wavelength between 100 nm and 280 nm for a first pre-determined period of time, to emit the wavelength between 280 nm and 315 nm for a second pre-determined period of time, and to emit the wavelength between 315 nm and 400 nm for a third pre-determined period of time, the second and third periods of time each being less than the first period of time.

According to one embodiment, a self-sterilizing system comprises a power source, and a sterilization assembly comprising a support housing, a plurality of light-emitting diodes coupled to the support housing, the plurality of light-emitting diodes being configured to selectively emit radiation having at least one wavelength between 100 nm and 400 nm, a controller coupled to the power source, the controller being configured to operate the plurality of light-emitting diodes by selectively providing power to the plurality of light-emitting diodes, and a power port coupled to the power source and the controller, the power port being configured to provide power to the controller.

In one example, the self-sterilizing system further comprises a motion detector coupled to the controller, the sterilization assembly further comprising an I/O port configured to be coupled to the motion detector, the controller further being configured to control the motion detector through the I/O port to detect motion within a proximity of the sterilization assembly, and in response to detecting the motion, cease providing power to the plurality of light-emitting diodes. In another example, the motion detector further comprises i) at least one passive infrared sensor (PIR) configured to detect infrared radiation within a field of view of the at least one PIR sensor, the controller is further configured to cease providing power to the plurality of light-emitting diodes in response to the detected infrared radiation, or ii) a capacitive sensor on a surface of the support housing configured to detect a user touching the capacitive sensor or being in a proximity to the capacitive sensor, the capacitive sensor being provided in addition to the at least one PIR sensor, the controller further configured to cease providing power to the plurality of light-emitting diodes in response to the capacitive sensor detecting the user.

In one example, the motion detector further comprises i) an ultrasonic transducer configured to emit an ultrasonic wave within a field of view of the transducer and detect the ultrasonic wave reflected from an object within the field of view of the transducer, the controller further configured to cease providing power to the plurality of light-emitting diodes in response to the reflected ultrasonic wave being detected, ii) a camera configured to acquire an image within a field of view of the camera, the controller further configured to cease providing power to the plurality of light-emitting diodes in response to processing the image, or iii) a capacitive sensor below a surface of the support housing and configured to detect a user touching the surface or being in a proximity to the capacitive sensor, the capacitive sensor being provided in addition to one of the ultrasonic transducer and the camera, the controller further configured to cease providing power to the plurality of light-emitting diodes in response to the capacitive sensor detecting the user.

In another example, the support housing has a circular shape configured to fit around a door knob and transmit the radiation onto a gripping surface of the door knob.

In one example, the support housing is constructed of a material configured to transmit the radiation from the plurality of light emitting diodes to a gripping surface of the sterilization assembly; and wherein the material is i) rigid or flexible and configured to expand to at least an outermost width of a surface of the gripping surface, and ii) transparent or translucent.

In another example, the self-sterilizing system further comprises a hinge configured to join a first section of the support housing to a second section of the support housing, and a separating connector configured to releasably attach the first section to the second section.

In one example, each of the plurality of light-emitting diodes is configured to selectively emit radiation having a wavelength between 100 nm and 280 nm, 280 nm and 315 nm, and/or a wavelength between 315 nm and 400 nm, and the controller is further configured to flash each the plurality of light-emitting diodes at each emitted wavelength for at least a pre-determined period of time.

In another example, at least one of plurality of light-emitting diodes is configured to selectively emit radiation having a wavelength between 100 nm and 280 nm, at least one of the plurality of light-emitting diodes is configured to selectively emit radiation having a wavelength between 280 nm and 315 nm, and at least one of the plurality of light-emitting diodes is configured to emit radiation having a wavelength between 315 nm and 400 nm, and the controller is further configured to emit the wavelength between 100 nm and 280 nm for a first pre-determined period of time, to emit the wavelength between 280 nm and 315 nm for a second pre-determined period of time, and to emit the wavelength between 315 nm and 400 nm for a third pre-determined period of time, the second and third periods of time each being less than the first period of time.

In one example, the power source is located externally to the support housing or the power source is located within the housing.

In another example, the power port is configured to be coupled to the external power source via a plurality of wires passed through a door or attached to a surface of the door.

Still other aspects, embodiments, and advantages of these exemplary aspects and embodiments are discussed in detail below. Embodiments disclosed herein may be combined with other embodiments in any manner consistent with at least one of the principles disclosed herein, and references to "an embodiment," "some embodiments," "an alternate embodiment," "various embodiments," "one embodiment" or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the disclosure. In the figures, each identical or nearly identical component that is illustrated in various figures may be represented by a like numeral. For purposes of clarity, not every component may be labeled in every figure. In the figures.

DETAILED DESCRIPTION

Due to the recent pandemic of the SARS-Cov-2 virus (i.e., Covid-19), there has been a growing need for devices to combat the spread of the virus. Passive sterilization disinfecting or sterilizing approaches have been implemented to prevent contact between a person and the virus. These approaches include the use of face masks and gloves to prevent the virus from leaving and/or entering the respiratory system of a person. Active sterilization on the other hand incorporates electronically-controlled components, such as the liquid spray described above. However, previous solutions using an active sterilization process suffer from several drawbacks.

In the case of the chemical spray type of active sterilization, the efficacy is reduced when the spray runs out. Furthermore, if the time between consecutive applications of the spray is not quick enough, then users may touch a contaminated surface before the next spray is emitted. Additionally, replenishing the chemical sprays used to disinfect surfaces produces waste. Another drawback of previous systems using active sterilization is radiation exposure. Some of these systems constantly bombard a surface with radiation selected at a wavelength intended to sterilize the surface. However, by constantly emitting the radiation, when a user engages with the surface, for example grasping a door handle, the user is exposed to the radiation. As used herein, the term "door handle" includes both round, knob-shaped grasping regions (i.e., door knobs) and elongated bar-shaped or lever grasping regions. Further, the term "door handle" can reference any type of mechanism used to open a door, including, without limitation latches, thumb turns and levers to name a few. What is needed is a solution to actively sterilize a target region often enough to prevent contamination by contact with the region, while also preventing unnecessary radiation exposure.

Figure 1:
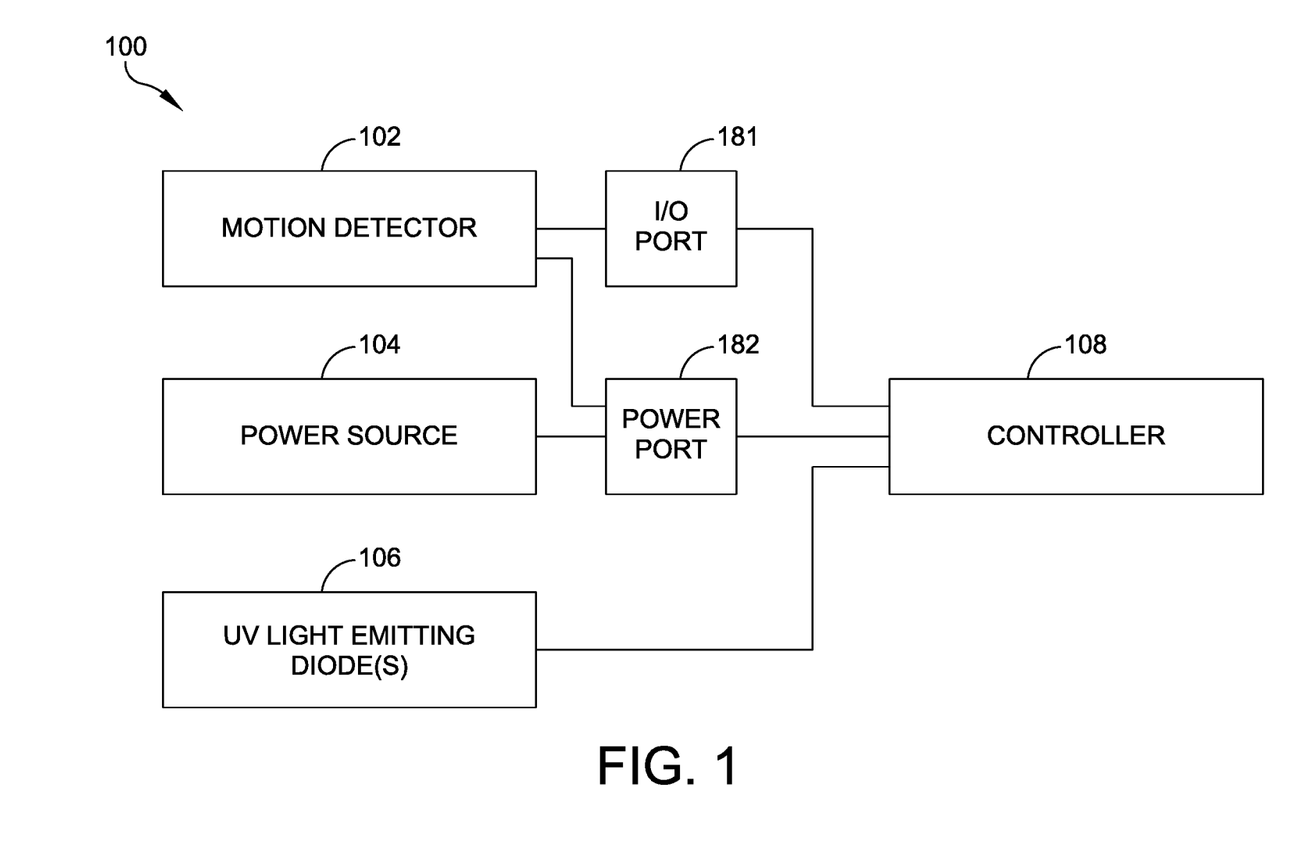
FIG. 1 is a block diagram of a circuit for controlling a plurality of light-emitting diodes according to an embodiment of the present disclosure.

Referring to FIG. 1, a circuit configured to detect a person about to touch an object and to clean the object is generally indicated at 100. As shown, the circuit 100 includes a motion detector 102, a power source 104, a plurality of UV light-emitting diodes (LEDs) 106, a controller 108, an I/O port 181, and a power port 182. The power port 182 is coupled to the power source 104 and the controller 108. The I/O port is coupled to the motion detector 102 and the controller 108, which in turn is coupled to each of the LEDs 106. The motion detector 102 is also coupled to the power port 182. According to certain examples, the power source 104 is a DC power source (e.g., a battery). In other examples, the power source is an AC power source (e.g., utility power). The I/O port 181 is configured to be decoupled from the motion detector 102 and the power port 182 is configured to be decoupled from the power source 104.

The controller 108 and any components thereof, is powered by the power source 104 when the controller is coupled to the power source 104 via the power port 182. The motion detector 102 receives power from the power source 104 via the power port 182 and communicates with the controller 108 via the I/O port 181. In certain examples, the controller 108 includes a microcontroller coupled to a UV LED controller board (not shown), which is coupled to each of the UV LEDs 106. In these examples, both the microcontroller and the UV LED controller board are coupled to the power source 104 via the power port 182 and the microcontroller is coupled to the motion detector 102 via the I/O port 181. Accordingly, the functionality of the controller 108 is achieved through the microcontroller in combination with the LED controller. Other embodiments are included herein, including embodiments where the microcontroller provides power to the UV LED controller and embodiments where the UV LED controller provides power to the microcontroller. Other combinations and modifications within the knowledge of one of ordinary skill in the art are contemplated herein.

To control the LEDs 106 simultaneously, in one example, each LED 106 is connected in parallel and power supplied by the controller 108 via the power source 104 is transferred to each LED 106 at approximately the same time. In another example, each LED 106 is individually coupled to the controller 108 such that the amount of power and exposure timing of each LED 106 is controlled. Other examples include combinations of parallel and individually-controlled LEDs 106.

One aspect of the motion detector 102 is to determine if a user is present within a proximity of a grasping region, door handle, or door knob that is being sterilized by the plurality of LEDs 106. In response to determining the presence of the user, the controller 108 ceases providing power to the plurality of LEDs 106, thereby preventing the user from being exposed to any radiation emitted by the plurality of LEDs 106.

In some examples, the motion detector 102 utilizes at least one passive infrared sensor (PIR) to detect infrared radiation within a field of view of the motion detector 102. In the case of multiple PIR sensors, in some examples, any PIR sensor of the multiple PIR sensors detecting motion is sufficient. In other examples, at least a predetermined number of the PIR sensors is required to positively indicate detected motion, for example, at least two PIR sensors.

To detect motion utilizing ultrasonic waves, some examples include an ultrasonic transducer in the motion detector 102 that emits an ultrasonic wave within a field of view of the transducer and detects the reflected ultrasonic wave from an object within the field of view, thereby providing data to the controller 108 to interpret as a distance to the object within the field of view.

To detect motion utilizing a bit-mapped image, some examples include a camera in the motion detector 102 that acquires one or more bit-mapped images for the controller 102 to process. In some examples, the camera includes a charge-coupled device (CCD) sensor. The controller 102 detects processes the one or more images by one of a plurality of techniques including detecting a face or body in an image, determining an apparent size of a finger, hand or body within an image, or tracking a change in apparent size of an object from one image to another. Other techniques for determining a need to cease irradiating a surface of a door handle or gripping surface before being engaged by a user are included in embodiments disclosed herein. In one embodiment, each of the plurality of LEDs 106 is one of a UVA, a UVB, or a UVC LED connected in parallel. In one example the plurality of LEDs 106 are UV-C LEDs, for example Rayvio XD UV LEDs connected in parallel and emitting a wavelength of 280 nm, the controller 108 is an Arduino Pro Mini coupled to a Rayvio UV Controller Board including a battery as the power source 104, and the motion detector 102 includes at least one passive infrared (PIR) motion sensor. Embodiments disclosed herein are not limited to these specific microcontrollers and LED controller boards. It is understood than embodiments herein include additional types of microcontrollers. For example, the controller 108 in certain embodiments is a programmable interface controller (PIC). Additional embodiments include customized hardware to act as the controller 108.

The amount of power provided to each of the one or more UV LEDs 106 is controlled by the controller 108. Various embodiments of a plurality of the UV LEDs 106 in the circuit 100 are contemplated herein. In one embodiment, each of the plurality of UV LEDs 106 emits the same wavelength of light (i.e., electromagnetic radiation) simultaneously. In an example, the wavelength is in the UVC region (i.e., 100 nm to 280 nm). In other embodiments, different subsets of the plurality of UV LEDs 106 emit different wavelengths to accomplish different functions. In an example, a first subset emits radiation in the UVC region and a second subset emits radiation in the UVA region (i.e., 315 nm to 400 nm). In another example, a third subset is added to emit radiation in the UVB region (i.e., 280 nm to 400 nm). Other combinations of subsets of the plurality of UV LEDs including two or more of the UVA, UVB, and UVC emitted wavelength regions are contemplated herein.

Each of the UVA, UVB, and UVC wavelength bands offers benefits to the application of disinfecting surfaces. However, in the particular scenario of disinfecting door handles or other surfaces in frequent contact with peoples' hands, the amount of time available to disinfect the targeted area (e.g., the grasping region, door knob, or door handle) affects the choice in wavelength. In an example, during longer exposure periods of disinfection (e.g., one or more minutes) the controller 108 operates the one or more UVC LEDs 106 to emit UVC radiation. In certain examples, a long exposure period is at least thirty minutes. According to certain examples, the one or more LEDs 106 remain powered and disinfecting the targeted area as long as AC power is available or until motion is detected. For shorter exposure periods, one or more of radiation in the UVA or UVB regions is flashed at a higher power, relative to the UVC exposure. In certain examples, a shorter exposure period is between 1 and 59 seconds.

To determine a suitable amount of available time for radiation exposure without emitting unnecessary radiation towards a person, for example when the person's hand is near a door handle, the motion detector 102 is utilized. While monitoring for an object within the field of view of the motion detector 102, the controller 108 is configured to obtain motion data from the motion detector 102 either continuously or in periodic samples. While the implementation of the type of sensor(s), hardware, and software to interpret the motion data may differ, one of ordinary skill in the art would understand how to accomplish the common goal of detecting motion to thereby turn off the one or more UV LEDs and thereby prevent unnecessary radiation from being emitted towards a person, and additionally minimizing power consumption.

An ultrasonic sensor measures the distance of a target object by emitting ultrasonic sound waves and converts the reflected sound at within a receiver's range (e.g., field of view) into an electrical signal. This electrical signal is interpreted by the controller 108 to calculate the distance between the sensor and the object. In response to the determined distance being less than a threshold, the controller 108 instructs the plurality of LEDs 106 to turn off. Since humans emit small amount of thermal radiation, a PIR motion sensor is used to detect changes in received radiation levels by providing an electrical signal to the controller 108 indicating an amount of change in radiation. Additional sensors for detection motion and/or a changing distance to an object are included in embodiments disclosed herein.

Figure 2A:
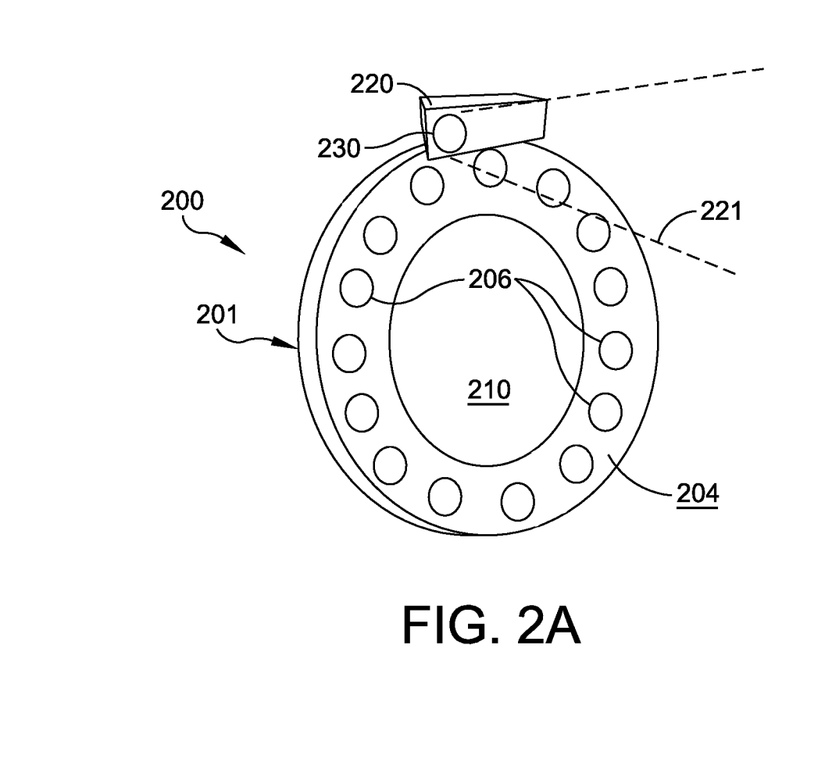
FIG. 2A is a front perspective view of a sterilization assembly according to an embodiment of the present disclosure.

Referring to FIG. 2A, a sterilization assembly is generally indicated at 200. The sterilization assembly 200 includes a support housing 201 having a front surface 204, a plurality of UV LEDs, each indicated at 206, a detection module 220, and an aperture 230 formed in the detection module 220. The support housing 201 has a circular shape and is constructed from an annular rigid material, thereby creating a central opening 210. In some examples, the material is a hard plastic. In other examples, the material is transparent or translucent to facilitate exposure of the radiation from the UV LEDs 206. Each of the plurality of UV LEDs 206 is configured to emit radiation at least in a direction towards an object protruding through the central opening 210. The aperture 230 is configured to permit the transmission and reception of sound waves, electromagnetic waves, or pulses thereof. In some examples, the aperture 230 is an empty space created by forming a cavity in the support housing 201. In other examples, the aperture 230 is a solid material, including one of glass or plastic, inserted into a cavity formed in the support housing 201.

The detection module 220 includes a motion detector and controller (e.g., similar to the motion detector 102 and the controller 108). In certain aspects, a circuit (e.g., similar to the circuit 100) is utilized to operate the plurality of UV LEDs 206 as well as the detection module 220 to monitor for objects within the proximity of the sterilization assembly 200. According to certain aspects, more than one detection module 220 is attached to the support to act as a motion detector. In some examples, two, three, or four or more detection modules 220 are attached to the support housing 201 to act as a motion detector with a greater field of view than a single detection module 220. The field of view 221 of the aperture 230 of the detection module 220 is shown in FIG. 2A.

To be fully self-contained as a device for sterilization of an object in the central opening 210 and able to receive radiation from the plurality of LEDs 206, the circuit (not shown) is entirely contained within the support housing 201 and the detection module 220. In a fully self-contained sterilization assembly 200, the power source is, in an example, a DC battery. Accordingly, in one example, the I/O port and the power port of the circuit 200 are located between the detection module and the support housing of the sterilization assembly 200. By having its own power source, the sterilization assembly 200 provides a benefit in the scenario where utility power is unavailable, yet gripping surfaces like door handles still require to be touched by people.

Figure 2B:
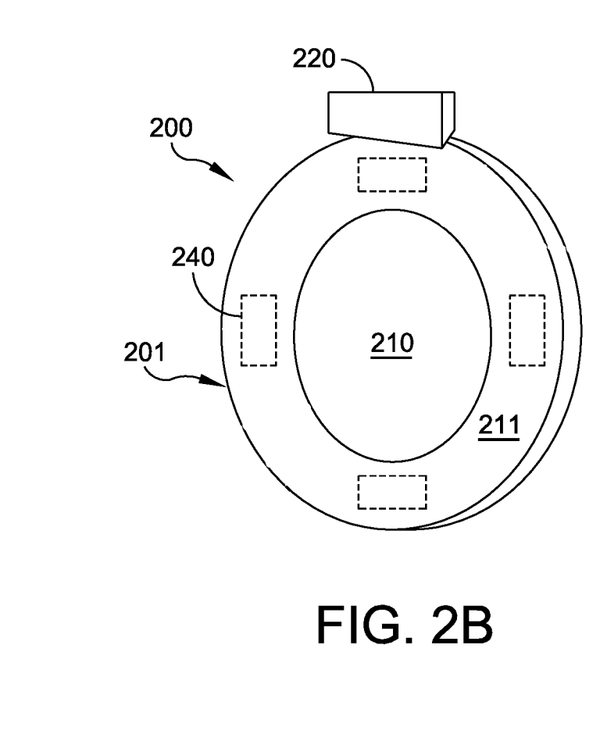
FIG. 2B is a rear perspective view of a sterilization assembly according to an embodiment of the present disclosure.

Referring to FIG. 2B, a plurality of adhesive pads, each indicated at 240, are provided to secure the sterilization assembly 200 to a surface, such as a door In one embodiment, the adhesive pads 240 are attached to the support housing 201 at a rear side 211 of the support housing. Alternatively, or in addition, the sterilization assembly is attached to the surface or door by including holes for screws, bolts or other fasteners.

Figure 2C:
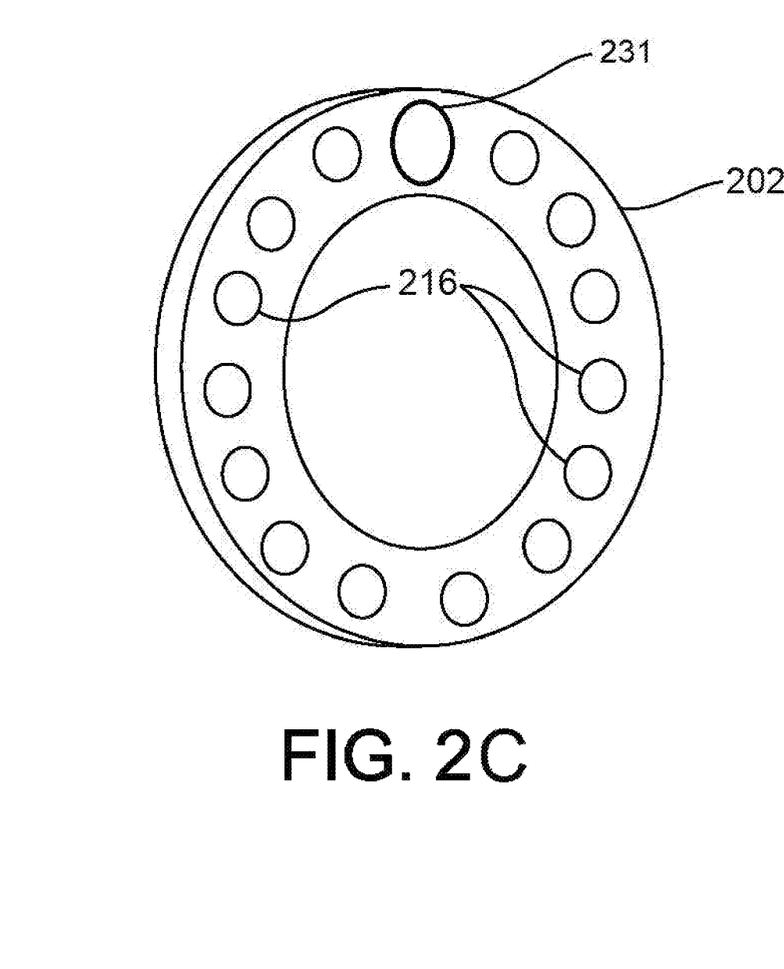
FIG. 2C is a front perspective view of a support housing according to an embodiment of the present disclosure.

To create a more compact design, certain embodiments include embedding a detection module within a support housing. In one embodiment, illustrated in FIG. 2C, a support housing 202 includes a plurality of LEDs 216. An aperture 231 is located in the support housing 202 at approximately the same radius from the center of the support housing 202 as the plurality of LEDs 216. The detection module in this embodiment is located within the support housing 202 behind the aperture 231. It is understood that this design modification is applicable to the sterilization assembly 200 as well as the sterilization assembly 300 discussed below.

Figure 2D:
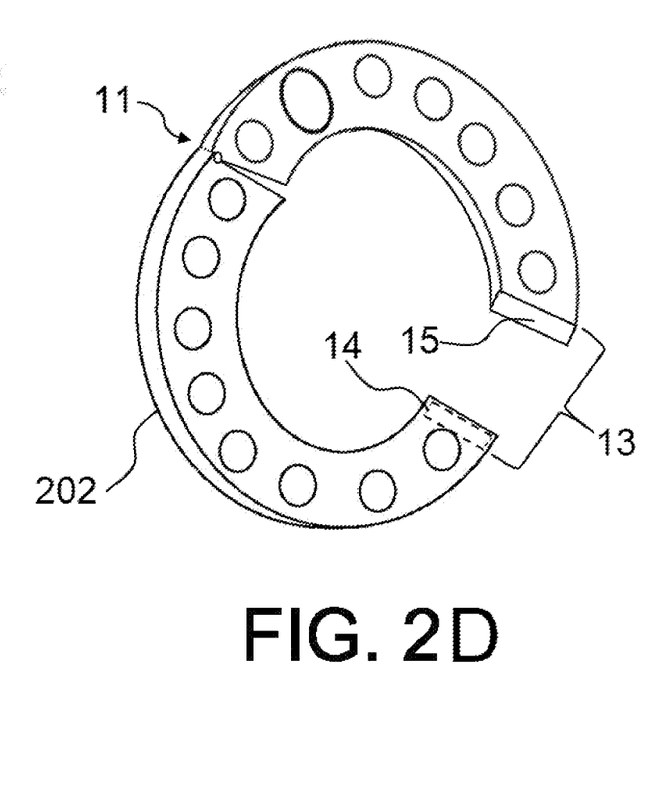
FIG. 2D is a front perspective view of a support housing including a hinge according to an embodiment of the present disclosure.

Additional embodiments include ring-shaped sterilization assemblies, e.g., similar to the sterilization assembly 200 as the sterilization assembly 300 discussed below, where the support housing includes a hinge configured to separate the support housing into two sections, thereby accommodating larger door handles. In an example, FIG. 2D illustrates an embodiment of a sterilization assembly 202 including a hinge 11 and a separating connector 13 (e.g., similar to the separating connector 12) that includes a first portion 14 and a second portion 15. The first portion 14 is configured to be releasably connected to the second portion 15 via one of: a pair of magnets, a pair of hook-and-loop fasteners, and a male flexible tab and a female fixed receptacle configured to receive the male tab. According to certain examples, the hinge 11 is a piano hinge. It is understood that embodiments include sterilization assemblies without hinges.

Figure 3A:
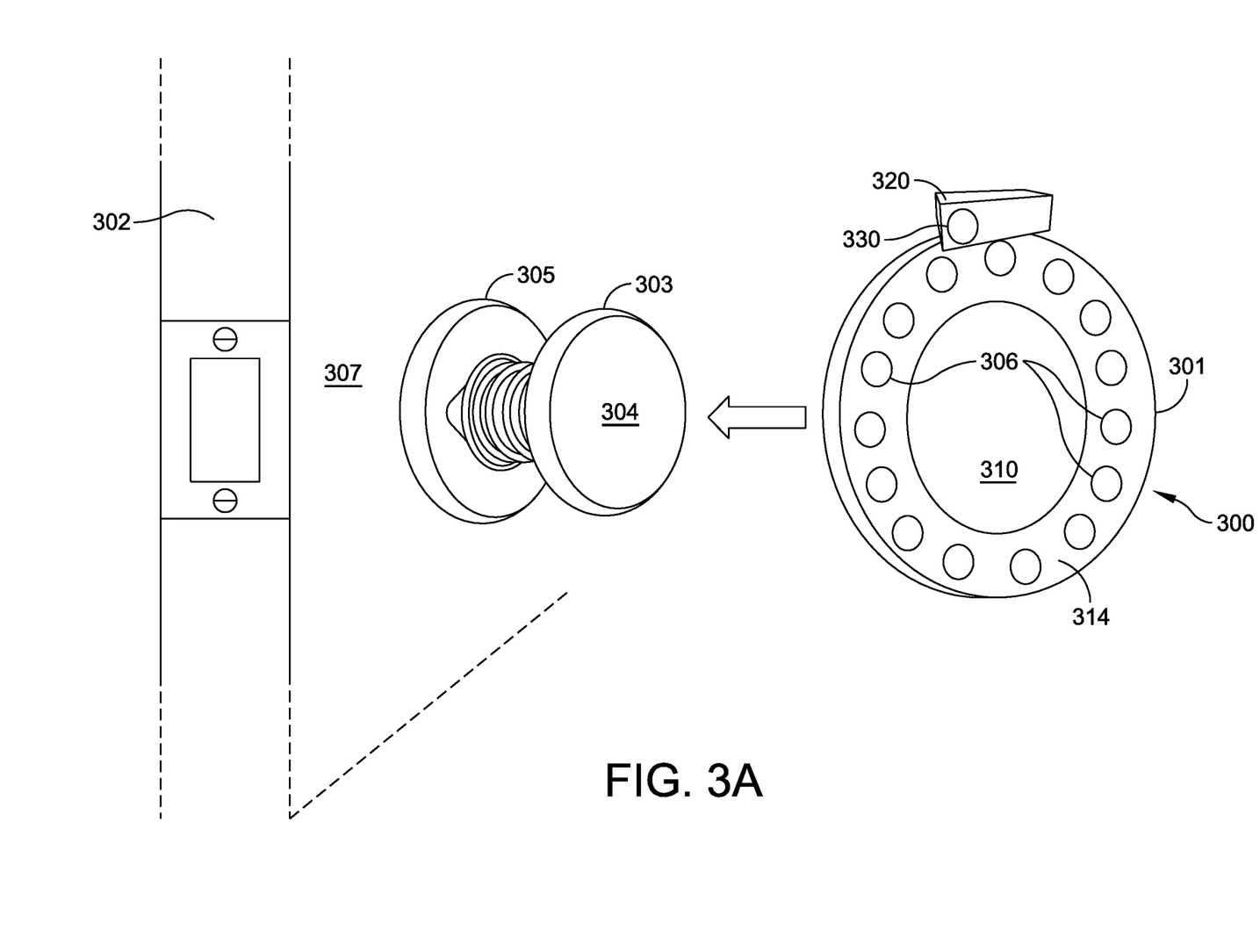
FIG. 3A is an exploded front perspective view of a self-sterilizing system prior to being installed on a door knob according to an embodiment of the present disclosure.
Figure 3B:
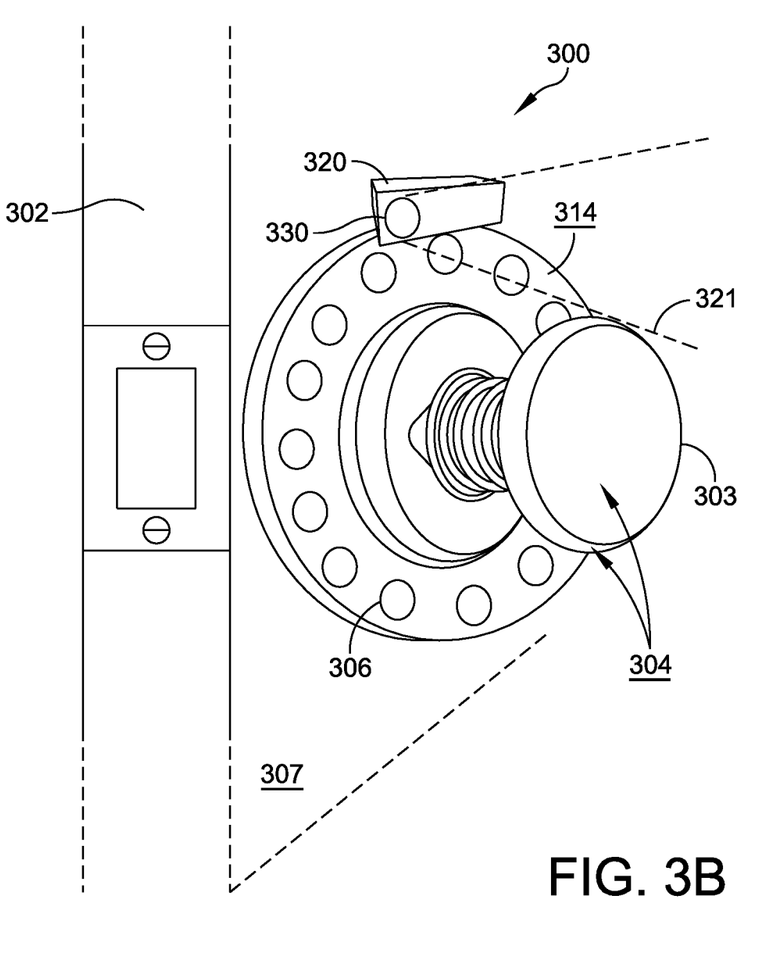
FIG. 3B is a front perspective view of a self-sterilizing system installed on a door knob according to an embodiment of the present disclosure.

FIG. 3A illustrates an installation of a sterilization assembly, generally indicated at 300, e.g., similar to the sterilization assembly 200, onto a door 302 that includes a door knob assembly 303. The sterilization assembly 300 includes a support structure 301 having a plurality of LEDs disposed within a front surface 314 and each indicated at 306. The support structure 301 is configured to have an opening 310 formed therein. The construction of the sterilization assembly 300 is similar to or nearly identical in construction as sterilization assembly 200. In one embodiment, the door knob of the door knob assembly 303 is secured to the door 302 in the traditional manner. To install the sterilization assembly 300, the opening 310 of the support structure 301 is passed over the door knob 304 and a rose 305 associated with the door knob assembly 303 to make contact with a surface 307 of the door 302. The support structure 301 is attached to the door 302 via one or more of adhesive or fasteners as described above with reference to sterilization assembly 200. The installation of the sterilization assembly 300 on the door knob assembly 303 of the door 302 is illustrated in FIG. 3B.

Once the sterilization assembly 300 is attached to the door 302, a field of view 321 of the aperture 330 is in a position for the detection module 320 to detect the presence of a hand or other object within a proximity of the door knob 304 of the door knob assembly 303. Until a hand or object is detected, the plurality of UV LEDs 306 emits radiation onto a gripping surface of the door knob 304. In response to detection of the hand or object, the plurality of UV LEDs 306 cease emitting UV radiation before contact is made between the hand or object and the gripping surface of the door knob 304.

According to certain embodiments, the sterilization assembly 300 is self-powered using a DC battery, as described above. In other embodiments, the sterilization assembly 300 receives AC power through a plurality of wires installed either within the door 302 or on a surface of the door 302. When utilizing AC power, the power port of the sterilization assembly is located on an external surface of the detection module 320 to permit connection to the wires providing AC power.

As an alternative to attaching the sterilization assembly 300 directly to the door 301, in one embodiment, the sterilization assembly 300 may be hung in between the rose 305 and the door knob 304 of the door knob assembly 303. According to certain embodiments, the rear side 211 of the support housing 201 does not contact the surface 301 of the door 302, thereby providing a portable sterilization assembly 300 that can easily be transferred from one door knob to another door knob. Embodiments herein include self-sterilizing systems including components located externally to a sterilization assembly (e.g., similar to the sterilization assembly 300). Such components include wires in or on the door 302 connecting the power port of the sterilization assembly to an external AC power source. It is understood that the sterilization assemblies and self-sterilizing systems described above are usable with lever-type door handles.

Other embodiments include a combination of AC and DC power. In an example, while AC power is available, additional power is provided to the plurality of UV LEDs 306, thereby increasing the efficacy of the sterilization of the gripping surface of the door knob 304 of the door knob assembly 303. In the event of a loss of AC power, or if the AC power is of poor quality, then internal DC power is utilized to continue the sterilization of the gripping surface 304.

Figure 4:
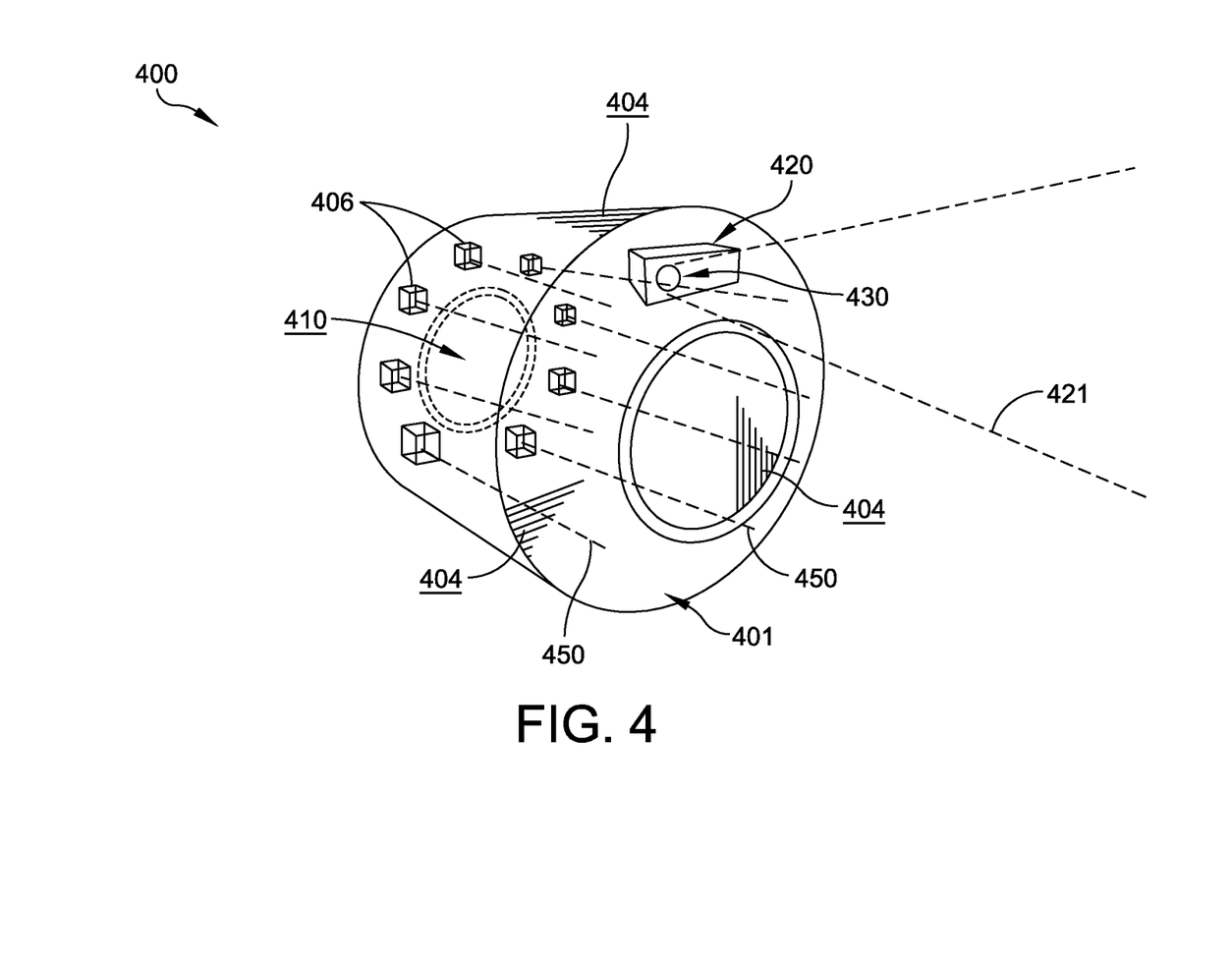
FIG. 4 is a front perspective view of a sterilization assembly according to an embodiment of the present disclosure.

Referring to FIG. 4, one embodiment of a sterilization assembly is generally indicated at 400. As shown, the sterilization assembly includes a gripping surface 404 of a support housing 401 containing a plurality of UV LEDs each indicated at 406, a plurality of light guides each indicated at 450, a detection module 420 having an aperture 430 with a field of view 421, and a rear opening 410. Each of the plurality of light guides 450 is configured to evenly transfer the focused light from a respective LED of the plurality of LEDs 406 towards the gripping surface 404.

The sterilization assembly 400 is constructed from a flexible material that is either entirely transparent or is translucent to thereby provide the UV light emitted from the plurality of LEDs 406 to be emitted through the gripping surface 404, thereby sterilizing it. To install the sterilization assembly 400, as illustrated in FIG. 4, the assembly 400 is pushed over a door knob assembly (e.g., similar to the door knob assembly 303 illustrated in FIG. 3A) through the rear opening 410. To detect if an object is within a proximity of the assembly 400, the detection module (e.g., similar to the detection module 220 and the detection module 320) is positioned with the assembly 400 such that the aperture 430 creates a field of view 421 for detecting motion. It is understood that embodiments disclosed herein include utilizing a plurality of detection modules 420 connected together to increase the detectable field of view, and furthermore, such embodiments include the aperture(s) 430 positioned in other directions than as illustrated in FIG. 4.

Figure 5A:
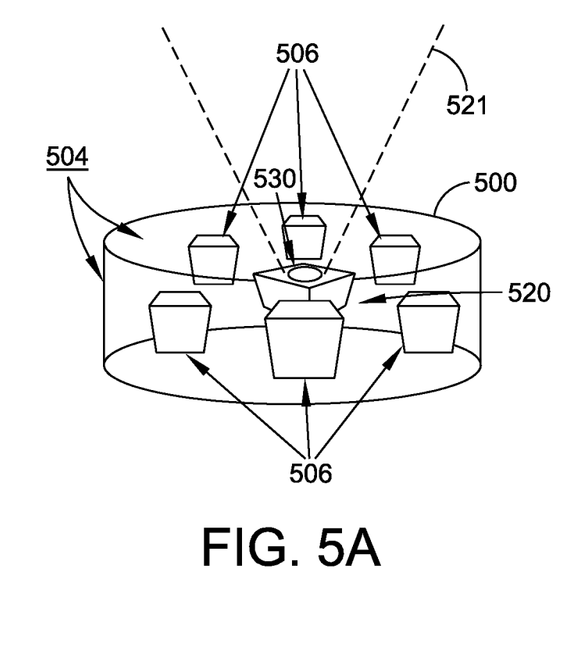
FIG. 5A is a side perspective view of a sterilization assembly according to an embodiment of the present disclosure.
Figure 5B:
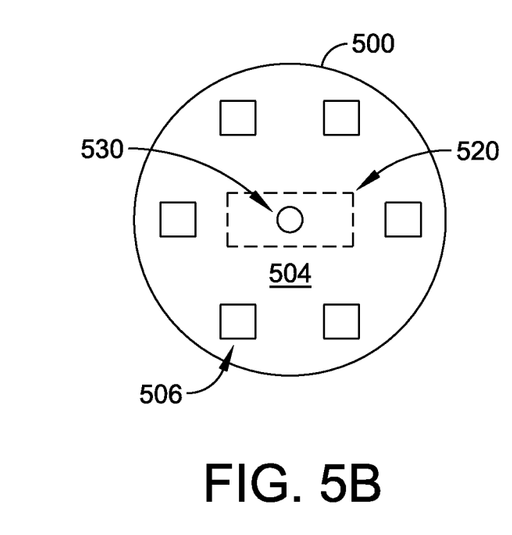
FIG. 5B is a top plan view of a sterilization assembly according to an embodiment of the present disclosure.
Figure 5C:
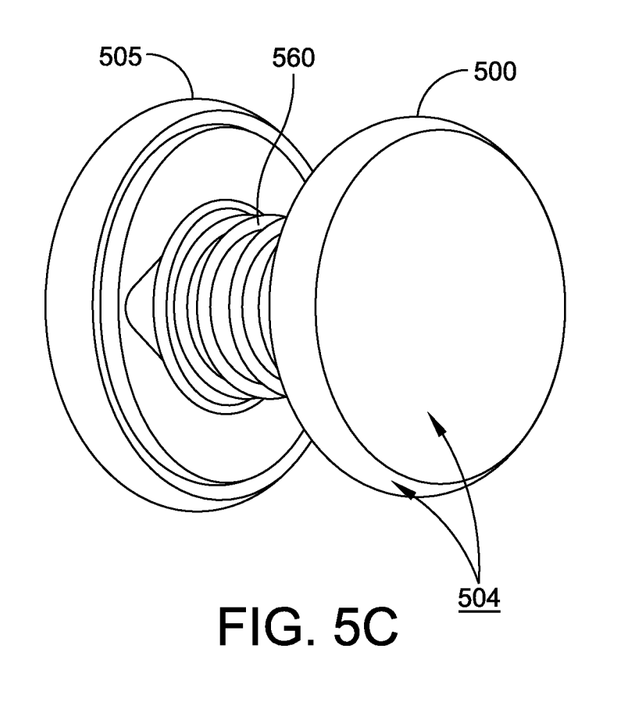
FIG. 5C is a front perspective view of a sterilization assembly according to an embodiment of the present disclosure.

FIG. 5A illustrates a side perspective view of a sterilization assembly generally indicated at 500, which is similar to the sterilization assembly 300 and the sterilization assembly 400. The sterilization assembly 500 includes a gripping body 504 having a plurality of UV LED diodes each indicated at 506 embedded therein. The sterilization assembly 500 further includes a detection module 520, and an aperture 530 formed in the detection module 520 and having a field of view 521, with the aperture 520 being in a position for the detection module 520 to detect the presence of a hand or other object within a proximity of the gripping body 504. Each of the UV LEDs 506 is configured to outwardly-emit UV radiation such that the gripping body 504 is sterilized. FIG. 5B illustrates the sterilization assembly 500 as seen from a top view along the central axis of the field of view 521 of the aperture 520. FIG. 5C illustrates the sterilization assembly 500 forming a door handle connected to a central body portion 560, which together rotate to unlock a door (e.g., similar to the door 302). In certain embodiments, the sterilization assembly 500, central body portion 560, and the rose 505 are constructed from a transparent or translucent material, either of which can be flexible or rigid. This material is configured to transmit light through at least the gripping surface 504, illustrated in FIG. 5C, to thereby disinfect the gripping surface 504. In some examples, the material is one of plastic, acrylic, glass, or synthetic rubber.

In the event of a failure or a false negative of the PIR sensor(s), transducer, camera, or other electronic device used to detect motion or human proximity according to any embodiment disclosed herein, a capacitive touch sensor is included in any sterilization assembly disclosed herein to provide a backup for the motion detector 102, e.g., coupled to the detection module 220, the detection module 320, the detection module 420, or the detection module 520. The capacitive sensor is located adjacent to and below a surface of the support housing that is capable of contacting a person's hand or fingers. In certain embodiments, the surface is one of the surface 204, the surface 314, the surface 404, and the surface 504.

Certain aspects provide the sterilization assembly 200, the sterilization assembly 300, the sterilization assembly 400 or the sterilization assembly 500 included in a self-sterilizing system similar to those described above, such that the assembly is connected to exterior components to receive AC power. In one embodiment, the self-sterilizing system includes one of the assemblies described above being connected to an exterior DC power source.

Additional applications and embodiments are disclosed herein. In an example, a portable sterilization assembly (e.g., similar to the sterilization assembly 300) is carried by a person to disinfect other surfaces besides a door handle, including but not limited to, a keyboard, a mouse, a desk, a tabletop, a chair, and a smart phone. While the figures depict round door handles, the same principles of the embodiments herein apply to lever door handles. In an example, a strip of UV LEDs (e.g., similar to the UV LEDs 506) is placed along the inside of a lever constructed from a transparent or translucent material as described above.

Having thus described several aspects of at least one embodiment, it is to be appreciated various alterations, modifications, and improvements will readily occur to those skilled in the art. Such alterations, modifications, and improvements are intended to be part of this disclosure and are intended to be within the scope of the disclosure. Accordingly, the foregoing description and drawings are by way of example only.

What is claimed is:

1. A sterilization assembly comprising:
   a support housing;
   a plurality of light-emitting diodes coupled to the support housing, the plurality of light-emitting diodes being configured to selectively emit radiation having at least one wavelength between 100 nm and 400 nm;
   a controller coupled to the plurality of light-emitting diodes, the controller being configured to operate the plurality of light-emitting diodes by selectively providing power to the plurality of light-emitting diodes;
   a power port coupled to a power supply and the controller, the port being configured to provide power to the controller; and
   a motion detector coupled to the controller and an I/O port coupled to the motion detector, the controller further being configured to control the motion detector through the I/O port to detect motion within a proximity of the sterilization assembly, and in response to detecting the motion, cease providing power to the plurality of light-emitting diodes,
   wherein the motion detector further comprises:
   i) at least one passive infrared sensor (PIR) configured to detect infrared radiation within a field of view of the at least one PIR sensor, the controller further configured to cease providing power to the plurality of light-emitting diodes in response to the detected infrared radiation; or
   ii) a capacitive sensor on a surface of the support housing configured to detect a user touching the capacitive sensor or being in a proximity to the capacitive sensor, the capacitive sensor being provided in addition to the at least one PIR sensor, the controller further configured to cease providing power to the plurality of light-emitting diodes in response to the capacitive sensor detecting the user.

2. A sterilization assembly comprising:
   a support housing;
   a plurality of light-emitting diodes coupled to the support housing, the plurality of light-emitting diodes being configured to selectively emit radiation having at least one wavelength between 100 nm and 400 nm;
   a controller coupled to the plurality of light-emitting diodes, the controller being configured to operate the plurality of light-emitting diodes by selectively providing power to the plurality of light-emitting diodes; and
   a power port coupled to a power supply and the controller, the port being configured to provide power to the controller,
   wherein the motion detector further comprises:
   i) an ultrasonic transducer configured to emit an ultrasonic wave within a field of view of the transducer and detect the ultrasonic wave reflected from an object within the field of view of the transducer, the controller further configured to cease providing power to the plurality of light-emitting diodes in response to the reflected ultrasonic wave being detected;
   ii) a camera configured to acquire an image within a field of view of the camera, the controller further configured to cease providing power to the plurality of light-emitting diodes in response to processing the image; or
   iii) a capacitive sensor provided below a surface of the support housing and configured to detect a user touching the surface or being in a proximity to the capacitive sensor, the capacitive sensor being provided in addition to one of the ultrasonic transducer and the camera, the controller further configured to cease providing power to the plurality of light-emitting diodes in response to the capacitive sensor detecting the user.

3. The sterilization assembly of claim 1 wherein the support housing has a circular shape configured to fit around a door knob and transmit the radiation onto a gripping surface of the door knob.

4. The sterilization assembly of claim 1 wherein the support housing is constructed of a material configured to transmit the radiation from the plurality of light emitting diodes to a gripping surface of the sterilization assembly; and wherein the material is:
   i) rigid or flexible and configured to expand to at least an outermost width of a surface of the gripping surface; and
   ii) transparent or translucent.

5. The sterilization assembly of claim 1 further comprising:
   a hinge configured to join a first section of the support housing to a second section of the support housing; and
   a separating connector configured to releasably attach the first section to the second section.

6. The sterilization assembly of claim 1 wherein each of the plurality of light-emitting diodes is configured to selectively emit radiation having a wavelength between 100 nm and 280 nm, 280 nm and 315 nm, and/or a wavelength between 315 nm and 400 nm; and
   the controller is further configured to flash each the plurality of light-emitting diodes at each emitted wavelength for at least a pre-determined period of time.

7. A sterilization assembly comprising:

a support housing;

a plurality of light-emitting diodes coupled to the support housing, the plurality of light-emitting diodes being configured to selectively emit radiation having at least one wavelength between 100 nm and 400 nm;

a controller coupled to the plurality of light-emitting diodes, the controller being configured to operate the plurality of light-emitting diodes by selectively providing power to the plurality of light-emitting diodes; and a power port coupled to a power supply and the controller, the port being configured to provide power to the controller, wherein at least one of plurality of light-emitting diodes is configured to selectively emit radiation having a wavelength between 100 nm and 280 nm, at least one of the plurality of light-emitting diodes is configured to selectively emit radiation having a wavelength between 280 nm and 315 nm, and at least one of the plurality of light-emitting diodes is configured to emit radiation having a wavelength between 315 nm and 400 nm; and wherein the controller is further configured to emit the wavelength between 100 nm and 280 nm for a first pre-determined period of time, to emit the wavelength between 280 nm and 315 nm for a second pre-determined period of time, and to emit the wavelength between 315 nm and 400 nm for a third pre-determined period of time, the second and third periods of time each being less than the first period of time.

8. A self-sterilizing system comprising:

a power source; and a sterilization assembly comprising a support housing;

a plurality of light-emitting diodes coupled to the support housing, the plurality of light-emitting diodes being configured to selectively emit radiation having at least one wavelength between 100 nm and 400 nm;

a controller coupled to the power source, the controller being configured to operate the plurality of light-emitting diodes by selectively providing power to the plurality of light-emitting diodes; and a power port coupled to the power source and the controller, the power port being configured to provide power to the controller; and a motion detector coupled to the controller, the sterilization assembly further comprising an I/O port configured to be coupled to the motion detector, the controller further being configured to control the motion detector through the I/O port to detect motion within a proximity of the sterilization assembly, and in response to detecting the motion, cease providing power to the plurality of light-emitting diodes, wherein the motion detector further comprises:

i) at least one passive infrared sensor (PIR) configured to detect infrared radiation within a field of view of the at least one PIR sensor, the controller further configured to cease providing power to the plurality of light-emitting diodes in response to the detected infrared radiation; or ii) a capacitive sensor on a surface of the support housing configured to detect a user touching the capacitive sensor or being in a proximity to the capacitive sensor, the capacitive sensor being provided in addition to the at least one PIR sensor, the controller further configured to cease providing power to the plurality of light-emitting diodes in response to the capacitive sensor detecting the user.

9. A self-sterilizing system comprising:

a power source; and a sterilization assembly comprising a support housing;

a plurality of light-emitting diodes coupled to the support housing, the plurality of light-emitting diodes being configured to selectively emit radiation having at least one wavelength between 100 nm and 400 nm;

a controller coupled to the power source, the controller being configured to operate the plurality of light-emitting diodes by selectively providing power to the plurality of light-emitting diodes; and a power port coupled to the power source and the controller, the power port being configured to provide power to the controller, wherein the motion detector further comprises:

i) an ultrasonic transducer configured to emit an ultrasonic wave within a field of view of the transducer and detect the ultrasonic wave reflected from an object within the field of view of the transducer, the controller further configured to cease providing power to the plurality of light-emitting diodes in response to the reflected ultrasonic wave being detected;

ii) a camera configured to acquire an image within a field of view of the camera, the controller further configured to cease providing power to the plurality of light-emitting diodes in response to processing the image; or iii) a capacitive sensor below a surface of the support housing and configured to detect a user touching the surface or being in a proximity to the capacitive sensor, the capacitive sensor being provided in addition to one of the ultrasonic transducer and the camera, the controller further configured to cease providing power to the plurality of light-emitting diodes in response to the capacitive sensor detecting the user.

10. The self-sterilizing system of claim 8 wherein the support housing has a circular shape configured to fit around a door knob and transmit the radiation onto a gripping surface of the door knob.

11. The self-sterilizing system of claim 8 wherein the support housing is constructed of a material configured to transmit the radiation from the plurality of light emitting diodes to a gripping surface of the sterilization assembly; and wherein the material is:

i) rigid or flexible and configured to expand to at least an outermost width of a surface of the gripping surface; and ii) transparent or translucent.

12. The self-sterilizing system of claim 8 further comprising:

a hinge configured to join a first section of the support housing to a second section of the support housing; and a separating connector configured to releasably attach the first section to the second section.

13. The self-sterilizing system of claim 8 wherein each of the plurality of light-emitting diodes is configured to selectively emit radiation having a wavelength between 100 nm and 280 nm, 280 nm and 315 nm, and/or a wavelength between 315 nm and 400 nm; and the controller is further configured to flash each the plurality of light-emitting diodes at each emitted wavelength for at least a pre-determined period of time.

14. A self-sterilizing system comprising:
a power source; and
a sterilization assembly comprising
   a support housing;
   a plurality of light-emitting diodes coupled to the support housing, the plurality of light-emitting diodes being configured to selectively emit radiation having at least one wavelength between 100 nm and 400 nm;
   a controller coupled to the power source, the controller being configured to operate the plurality of light-emitting diodes by selectively providing power to the plurality of light-emitting diodes; and
   a power port coupled to the power source and the controller, the power port being configured to provide power to the controller,
   wherein at least one of plurality of light-emitting diodes is configured to selectively emit radiation having a wavelength between 100 nm and 280 nm, at least one of the plurality of light-emitting diodes is configured to selectively emit radiation having a wavelength between 280 nm and 315 nm, and at least one of the plurality of light-emitting diodes is configured to emit radiation having a wavelength between 315 nm and 400 nm; and
   wherein the controller is further configured to emit the wavelength between 100 nm and 280 nm for a first pre-determined period of time, to emit the wavelength between 280 nm and 315 nm for a second pre-determined period of time, and to emit the wavelength between 315 nm and 400 nm for a third pre-determined period of time, the second and third periods of time each being less than the first period of time.

15. The self-sterilizing system of claim 8 wherein the power source is located externally to the support housing or the power source is located within the housing.

16. The self-sterilizing system of claim 15 wherein the power port is configured to be coupled to the external power source via a plurality of wires passed through a door or attached to a surface of the door.

* * * * *